US009681995B2

(12) United States Patent
Takeuchi et al.

(10) Patent No.: US 9,681,995 B2
(45) Date of Patent: Jun. 20, 2017

(54) APPARATUS FOR MANUFACTURING ABSORBENT ARTICLES AND METHOD FOR MANUFACTURING ABSORBENT ARTICLES

(71) Applicant: UNICHARM CORPORATION, Shikokuchuo-shi, Ehime (JP)

(72) Inventors: Kenji Takeuchi, Kanonji (JP); Taizo Horiwaki, Kanonji (JP)

(73) Assignee: UNICHARM CORPORATION, Ehime (JP)

( * ) Notice: Subject to any disclaimer, the term of this patent is extended or adjusted under 35 U.S.C. 154(b) by 91 days.

(21) Appl. No.: 14/403,508

(22) PCT Filed: May 31, 2013

(86) PCT No.: PCT/JP2013/065175
§ 371 (c)(1),
(2) Date: Nov. 24, 2014

(87) PCT Pub. No.: WO2013/180262
PCT Pub. Date: Dec. 5, 2013

(65) Prior Publication Data
US 2015/0111714 A1    Apr. 23, 2015

(30) Foreign Application Priority Data
May 31, 2012  (JP) .................. 2012-124896

(51) Int. Cl.
*B31B 49/00* (2006.01)
*A61F 13/15* (2006.01)

(52) U.S. Cl.
CPC .. *A61F 13/15577* (2013.01); *A61F 13/15593* (2013.01); *A61F 13/15764* (2013.01); *A61F 13/15772* (2013.01)

(58) Field of Classification Search
CPC .......... A61F 13/15577; A61F 13/15593; A61F 13/15764; A61F 13/15772
(Continued)

(56) References Cited

U.S. PATENT DOCUMENTS 4,233,331 A * 11/1980 Lemke ................ B21D 51/383
156/332
4,726,876 A *  2/1988 Tomsovic, Jr. ... A61F 13/15601
156/552
(Continued)

FOREIGN PATENT DOCUMENTS

EP           1162162 A1   12/2001
JP      2005-298194 A    10/2005
(Continued)

OTHER PUBLICATIONS

International Search Report mailed Aug. 13, 2013 in International Application No. PCT/JP2013/065175, filed May 31, 2013.
(Continued)

*Primary Examiner* — Sameh Tawfik
(74) *Attorney, Agent, or Firm* — Hauptman Ham, LLP (57) ABSTRACT

An apparatus includes a rotary drum for disposing a workpiece on a web and a web position guiding mechanism for guiding a position of the web. The rotary drum includes a suction unit for sucking the workpiece. The suction unit is configured to change a disposition direction of the workpiece from a first disposition direction at the reception point to a second disposition direction at a delivery point. An external shape of the workpiece sucked by the suction unit is an external shape in which an outer edge portion of the workpiece is close to a rotary shaft side of the rotary drum. At an abutment point, a central portion of the workpiece and the web come into contact with each other. At the delivery point, the web is disposed so that an outer edge portion of
(Continued)

the workpiece and the web come into contact with each other.

6 Claims, 8 Drawing Sheets

(58) Field of Classification Search
 USPC .......................................................... 493/374
 See application file for complete search history.

(56) References Cited

U.S. PATENT DOCUMENTS

| | | | |
|---|---|---|---|
| 6,915,829 B2* | 7/2005 | Popp | A61F 13/15577 156/263 |
| 7,569,007 B2* | 8/2009 | Thoma | B65H 45/162 493/11 |
| 9,237,970 B2* | 1/2016 | Iida | A61F 13/15723 |
| 2002/0123417 A1* | 9/2002 | Cote | B65H 23/048 493/34 |
| 2010/0122766 A1* | 5/2010 | Yamamoto | A61F 13/15723 156/290 |

FOREIGN PATENT DOCUMENTS

| | | |
|---|---|---|
| JP | 2010-115427 A | 5/2010 |
| JP | 2011-030804 A | 2/2011 |
| JP | 2012-024242 A | 2/2012 |

OTHER PUBLICATIONS

Extended European Search Report in EP Application No. 13796866.5, dated Dec. 8, 2015.
Office Action in ID Application No. P-00201407972, mailed Mar. 21, 2017, for which an English abstract is attached.

* cited by examiner

APPARATUS FOR MANUFACTURING ABSORBENT ARTICLES AND METHOD FOR MANUFACTURING ABSORBENT ARTICLES

RELATED APPLICATIONS

The present application is a National Phase of International Application Number PCT/JP2013/065175, filed May 31, 2013, which claims priority to Japanese Application Number 2012-124896, filed May 31, 2012.

TECHNICAL FIELD

The present invention relates to an apparatus for manufacturing absorbent articles and a method for manufacturing absorbent articles, each of which includes a rotary drum at which there is provided a suction unit for sucking a workpiece that is a constituent element constituting a part of an absorbent article.

BACKGROUND ART

As a method for manufacturing absorbent articles, there is employed a method for conveying a web constituting an exterior body of a disposable diaper in a continuous state, disposing an elastic member constituting a leg gather on this web in an expanded state, and joining with the web and a workpiece that is an absorbent main body having an absorber absorbing a bodily liquid (for example, refer to Patent Literature 1).

In addition, for the convenience of manufacture, a web constituting an exterior body is conveyed in a continuous state in a widthwise direction of the absorbent article. On the other hand, a workpiece is manufactured in a continuous state in a longitudinal direction of an absorbent article, the manufactured workpiece is cut in an individual product length, and thereafter, the cut workpiece is disposed on the web. At this time, in order to align a direction of the workpiece and the web, the workpiece is rotated at an angle of 90 degrees, and thereafter, the rotated workpiece is disposed on the web (for example, refer to Patent Literature 2).

A rotational mechanism for the workpiece described in Patent Literature 2 is provided with a rotary drum and a plurality of suction units that are provided on an outer periphery of the rotary drum. The suction unit conveys workpieces upward of the web while the workpieces are rotated in a state in which the workpieces are sucked on a one-by-one pieces basis and then the workpieces are disposed at a predetermined position of the web. A suction face of the suction unit rotating on the outer periphery of the rotary drum restrains a difference in circumferential speed at the time of receipt of a workpiece and thus it is preferable to maintain a distance from a rotary shaft of the rotary drum. Therefore, the suction face is formed in a shape in which at least an outer edge portion of the suction face is inclined to a rotary shaft side of the rotary drum in comparison with a central portion of the suction face.

However, if the outer edge portion of the suction face is inclined to the rotary shaft side of the rotary drum, a gap between the outer edge portion of the workpiece and the web is produced at the time of delivery of the workpiece to the web. Therefore, the manufacturing apparatus of Patent Literature 2 is provided with a web position guiding mechanism to guide a web position so that both end portions in the cross direction of the web approaches a workpiece more significantly than a center in a cross direction at a position of delivering the workpiece to the web.

CITATION LIST

Patent Literature

[PTL 1]
Japanese Unexamined Patent Application Publication No. 2011-30804
[PTL 2]
Japanese Unexamined Patent Application Publication No. 2010-115427

SUMMARY OF INVENTION

However, the conventional manufacturing methods described above entail the following problems.

The manufacturing method described in Patent Literature 1 is to dispose a workpiece on a web while conveying a continuous web on which an elastic member is disposed. On a continuum, an elastic member displaced in a cross direction crossing a conveyance direction is disposed in a wavy shape. In the continuum, there exist a portion contracted by the elastic member and a portion that is not contracted by the elastic member, and this continuum is not uniformly contracted as a whole. Therefore, a position in the cross direction of the continuum is partially shifted, and there is an apprehension that a position of mounting a workpiece may be shifted.

In particular, as in the manufacturing apparatus described in Patent Literature 2, if positioning is performed at an outer edge portion of a workpiece to the exclusion of a central portion of the workpiece, a position of the entire workpiece may be shifted according to a position of the outer edge portion of the workpiece. Further, if one position of the outer edge portion of the workpiece is shifted, a wrinkle or a twist may occur with a web positioned at the central portion of the workpiece.

Accordingly, the present invention has been made in view of such a circumstance, and it is an object of the present invention to provide an apparatus for manufacturing absorbent articles and a method for manufacturing absorbent articles which are capable of transferring an workpiece while restraining an occurrence of a wrinkle or a twist in the case of adhering a workpiece such as an absorbent main body on a web to be continuously conveyed.

Solution to Problem

In order to resolve the above problem, the apparatus for manufacturing absorbent articles according to the present disclosure is summarized as the apparatus for manufacturing absorbent articles including: a workpiece disposition mechanism that disposes a workpiece which is a constituent element constituting a part of an absorbent article on a sheet-shaped continuous web on which an elastic member expanded in a conveyance direction of the web and in a cross direction crossing the conveyance direction is disposed; and a web position guiding mechanism that guides a position of the web, wherein the workpiece disposition mechanism comprises a rotary drum having a suction unit sucking the workpiece; the suction unit is constituted so as to suck the workpiece at a reception point of the workpiece, change a disposition direction of the workpiece from a first disposition direction of the workpiece at the reception point to a second disposition direction of the workpiece at a delivery point of the workpiece onto the web while the rotary drum is rotated, and dispose the workpiece sucked by the suction unit onto the web, in a cross section taken along the second disposition direction of the suction unit at the delivery point, an external shape of the workpiece sucked by the suction unit is an external shape in which an outer edge portion of the workpiece is close to a rotary shaft side of the rotary drum in comparison with a central portion of the workpiece, and the web position guiding mechanism is a guiding mechanism in which at an abutment point on an upstream side in a conveyance direction more significantly than the delivery point, the web is disposed so that a central portion of the workpiece and the web come into contact with each other and an outer edge portion of the workpiece is spaced from the web, and at the delivery point, the web is disposed so that an outer edge portion of the workpiece and the web come into contact with each other.

The method for manufacturing absorbent articles according to the present disclosure is summarized as the method for manufacturing absorbent articles including a workpiece disposition step of, by a rotary drum at which a suction unit sucking the workpiece is provided, disposing a workpiece which is a constituent element constituting a part of an absorbent article on a sheet-shaped continuous web on which an elastic member expanded in a conveyance direction of the web and in a cross direction crossing the conveyance direction is disposed, the workpiece disposition step comprising: a workpiece rotation step of sucking the workpiece at a reception point of the workpiece for the rotary drum to receive the workpiece, and converting a disposition direction of the workpiece from a first disposition direction of the workpiece at the reception point to a second disposition direction of the workpiece at a delivery point of the workpiece onto the web; and a workpiece delivery step of delivering, onto the web, the workpiece sucked by the suction unit at the delivery point, the workpiece rotation step conveying the workpiece so that an outer edge portion of the workpiece sucked by the suction unit in a cross section taken along the second disposition direction at the delivery point is close in comparison with a central portion of the workpiece, the workpiece disposition step including: a first guiding step of disposing the web so that an outer edge portion of the workpiece and the web come into contact with each other at the delivery point; and a second guiding step of, at an abutment point on an upstream side in a conveyance direction more significantly than the delivery point, disposing the web so that an outer edge portion of the workpiece is spaced from the web and a central portion of the workpiece and the web come into contact with each other.

DESCRIPTION OF EMBODIMENTS

Hereinafter, an apparatus for manufacturing absorbent articles and a method for manufacturing absorbent articles, according to the present invention, will be described with reference to the drawings. Specifically, a description will be given with respect to: (1) Structure of Absorbent Article; (2) Method for Manufacturing Absorbent Articles; (3) Structure of Apparatus for Manufacturing Absorbent Articles; (4) Operation of Apparatus for Manufacturing Absorbent Articles; Functions; (5) Advantageous Effects; and (6) Other Embodiments.

In the following description of the drawings, same or similar constituent elements are designated by same or similar reference numerals. However, it is to be kept in mind that the drawings are merely schematic, and rates or the like of the respective dimensions are different from real ones. Therefore, specific dimensions or the like should be determined in consideration of the following description. In addition, it is a matter of course that among the respective drawings as well, portions with different dimensional relationship or rates are included.

(1) Structure of Absorbent Article

Figure 1:
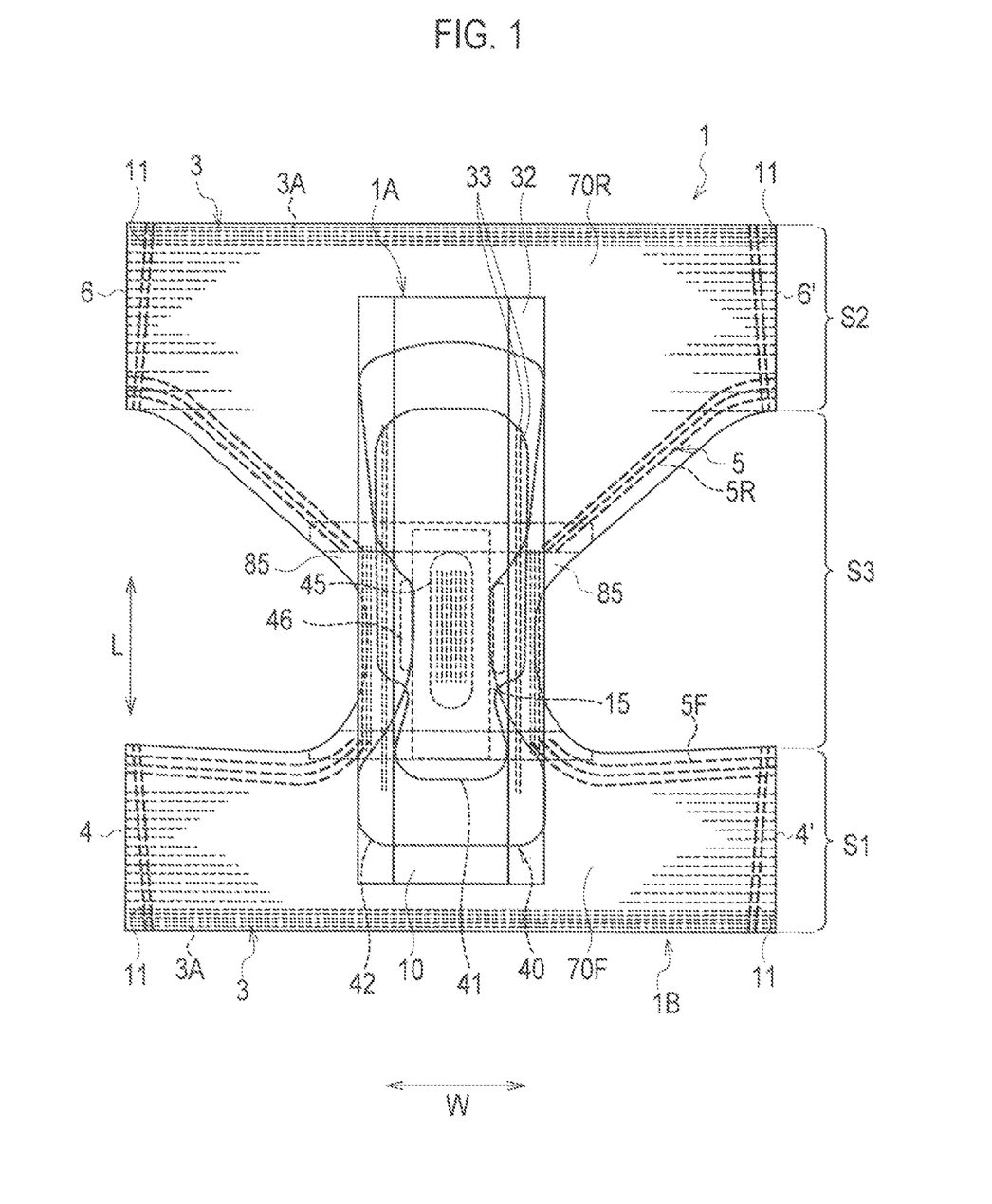
FIG. 1 is an exploded plan view of an absorbent article according to an embodiment.

First, a structure of an absorbent article 1 according to the embodiment will be described with reference to the drawings. FIG. 1 is an exploded plan view showing a state in which the absorbent article 1 according to the embodiment is exploded. In the embodiment, the absorbent article 1 is a disposable diaper of a pants type. It should be noted that the exploded plan view of FIG. 1 is diagram in which leg-line elastic member and hipline elastic member are in an expanded state such that wrinkles are not formed in an exterior body, for example, that configure the absorbent article 1.

In the embodiment, the pants-type disposable diaper is a diaper formed in advance in the pants type. It is to be noted that in the embodiment, the above disposable diaper is constituted so as to manufacture the disposable diaper of the pants type, whereas the disposable diaper may be constituted so as to manufacture a disposable diaper of an open type. The disposable diaper of the open type is a disposable diaper in which the diaper is opened in a state before use, and predetermined portions of the product are fastened with each other by attachment tape or the like to thereby attach to a user.

The absorbent article 1 has a longitudinal direction L extending to a body foreside and a body backside of a wearer and a widthwise direction W that is orthogonal to the longitudinal direction L.

The absorbent article 1 has a front waistline region S1 corresponding to a front waistline of a wearer, a back waistline region S2 corresponding to a back waistline of the wearer, in a longitudinal direction L of the absorbent article 1, and a crotch region S3 corresponding to a crotch of the wearer and positioned between the front waistline region S1 and the back waistline region S2.

A front waistline edge portion 4 lying outside in one widthwise direction of the absorbent article 1 in the front waistline region S1 is joined with a back waistline edge portion 6 lying outside in one widthwise direction of the back waistline region S2, and a front waistline edge portion 4' lying outside in the other widthwise direction is joined with a back waistline edge portion 6' lying outside in the other widthwise direction, whereby the absorbent article 1 is formed in the pants type. In the front waistline region S1 and the back waistline region S2 of the disposable diaper of the pants type, a joint unit 11 of which the respective edge portion s are joined with each other is formed, and the crotch region S3 is a region inner side than the joint unit 11 in the longitudinal direction.

In the absorbent article 1, a hipline opening unit disposed so as to surround a hip of a wearer and one pair of leg hole opening units disposed so as to surround legs of the wearer are formed in a state in which these opening units are formed in the pants type. A leg hole opening unit is a portion which, in the crotch region S3, is concaved inner side in a widthwise direction than an outside end of a front waistline region in the widthwise direction and an outside end of a back waistline region in the widthwise direction. The periphery of the leg hole opening unit is equivalent to the leg-line portion.

The absorbent article 1 includes: an absorbent main body 1A including a topsheet 10 and an absorber 40 or the like; and an exterior body 1B including a foreside exterior topsheet 70F, a backside exterior topsheet 70R, a foreside exterior backsheet 80F, and a backside exterior backsheet 80R or the like. These constituent elements are joined with each other by an adhesive or thermal fusion deposition, for example.

The exterior body 1B constitutes an exterior portion of the absorbent article 1. The exterior body 1B is disposed at a non-skin contact surface side from the absorbent main body 1A. The foreside exterior topsheet 70F and the foreside exterior backsheet 80F are disposed across the front waistline region S1 and the crotch region S3. The backside exterior topsheet 70R and the backside exterior backsheet 80R are disposed across the back waistline region S2 and the crotch region S3. The foreside exterior topsheet 70F and the foreside exterior backsheet 80F and the backside exterior topsheet 70R and the backside exterior backsheet 80R are disposed so as to be spaced in the longitudinal direction, and are coupled to each other by an intermediate exterior sheet 85.

The absorbent main body 1A includes a topsheet 10, a second sheet 15, an absorber backside sheet, and a leakage preventing unit, and is disposed on a wearer's side from the exterior body 1B.

The topsheet 10 is a sheet to form a skin contact surface that is capable of directly coming into contact with a skin of a wearer. The topsheet 10 is disposed on the skin contact surface side from an absorber 40. The topsheet 10 is formed of a liquid permeable sheet such as a hydrophilic unwoven cloth or fiber, an opening plastic film, an opening hydrophobic unwoven cloth.

A second sheet 15 is joined with a non-skin contact surface side of the topsheet 10.

The second sheet 15 is disposed between the topsheet 10 and the absorber 40.

An absorber 40 is disposed between a composite sheet on which a topsheet 10 and a second sheet 15 are joined with each other and an absorber backside sheet (not shown). The absorbent main body 1A is disposed at least at a center in a widthwise direction of a crotch region S3. The absorber 40 is formed of mixture powder such as a powdered pulp or a highly absorbent polymer. The absorber 40 is made of a first absorption layer 41 positioned on a non-skin contact surface side and a second absorption layer 42 overlapped on the first absorption layer 41 and positioned on a skin contact surface side of a wearer.

In the first absorption layer 41, a central slit 45 and a side slit 46, both of which extend in the longitudinal direction, are formed. The side slit 46 is formed outer side in the widthwise direction than the central slit 45. The absorber 40 is constituted so as to be deformed due to the central slit or side slit formed in the absorber 40, when the absorbent article 1 is worn.

The leakage preventing unit has a leakage preventing side sheet 32 and a leakage preventing elastic member 33, and is disposed along the longitudinal direction at widthwise end portions of the absorbent main body 1A. The leakage preventing side sheet 32 is provided so as to integrally envelope the topsheet 10 and the absorber backside sheet at both side ends in the widthwise direction W of the absorber 40. The leakage preventing side sheet 32 is formed of a sheet such as a liquid impermeable unwoven cloth. One end portion in the widthwise direction of the leakage preventing side sheet 32 is joined with the non-skin surface side of the absorber backside sheet, and the other end portion in the widthwise direction of the leakage preventing side sheet 32 is folded back from the lateral side in the widthwise direction of the absorber 40, and is joined with the skin contact surface of the topsheet 10.

The leakage preventing side sheet 32 is joined with a topsheet or the like by a hot melt adhesive. The leakage preventing elastic member 33 is adhered in an expanded state between the absorber backside sheet and the leakage preventing side sheet 32. The leakage preventing elastic member 33 respectively contracts in the longitudinal direction both end portions in the widthwise direction of the absorber.

In the front waistline region S1 and the back waistline region S2, a waist gather 3 is provided. The waist gather 3 has an elongated hipline elastic member 3A such as a synthetic rubber arranged so as to expand and contract along the widthwise direction W. The waist gather 3 is continuous from one front waistline edge portion 6' lying outside in the widthwise direction W of the absorbent article 1 in the front waistline edge portion 4 up to the other front waistline edge portion 4' and is continuous from one back waistline edge portion 6 lying outside in the widthwise direction W of the absorbent article 1 in the back waistline region S2 up to the back waistline edge portion 6'.

At the periphery of the leg hole opening unit, a leg gather 5 is provided. At least a part of the leg gather 5 is disposed along the leg hole opening unit. The leg gather 5 is formed of a front leg-line elastic member 5F disposed in the front waistline region S1 and a back leg-line elastic member 5R disposed across the back leg-waistline region S2 and the crotch region S3.

The front leg-line elastic member 5F and the hipline elastic member 3A are disposed between the foreside exterior topsheet 70F and the foreside exterior backsheet 80F, and the back leg-line elastic member 5R and the hipline elastic member 3A are disposed between the backside exterior topsheet 70R and the backside exterior backsheet 80R. The steps of disposing the hipline elastic member 3A, the front leg-line elastic member 5F, and the back leg-line elastic member 5R will be described later in detail.

(2) Method for Manufacturing Absorbent Articles

Figure 2:
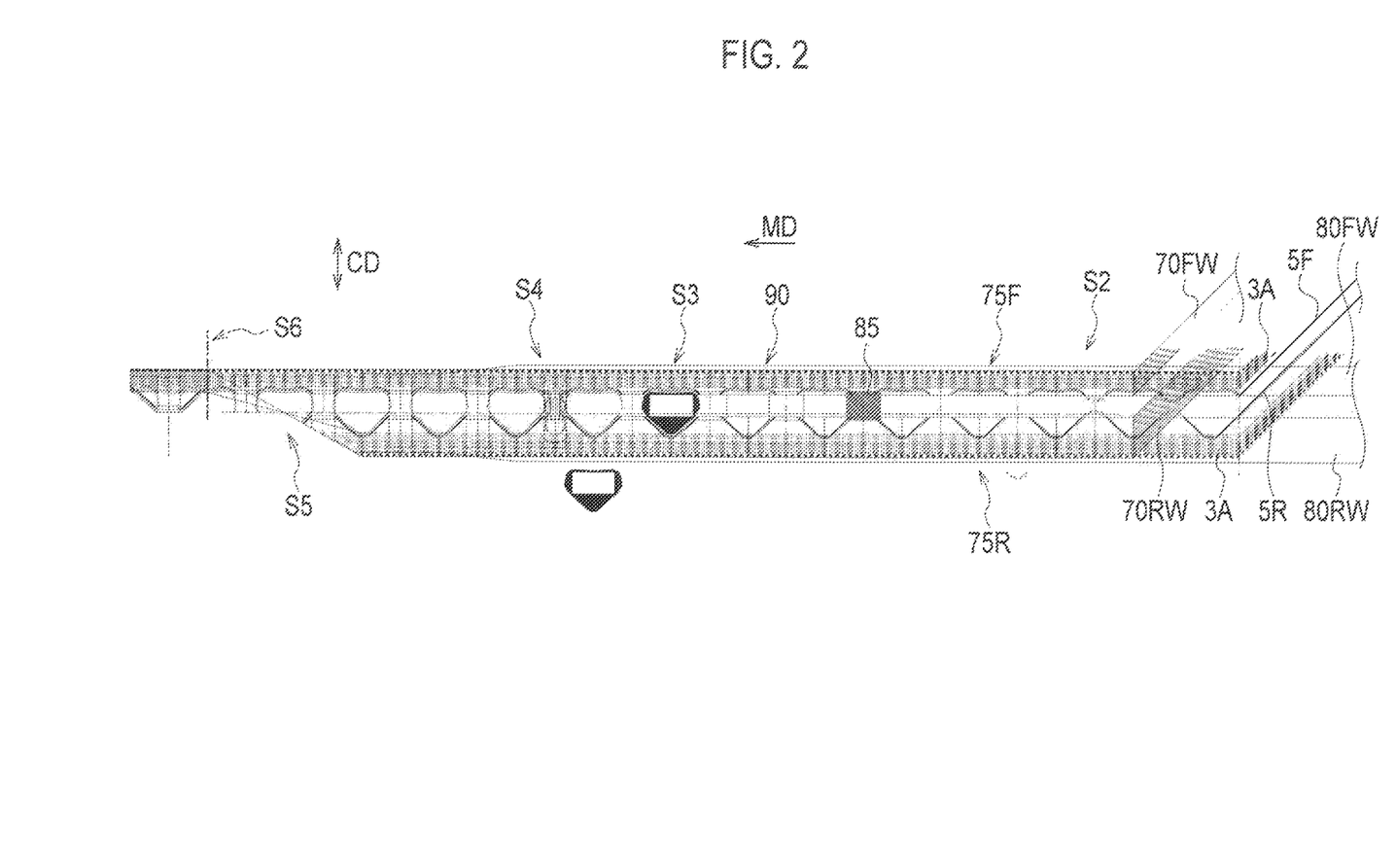
FIG. 2 is a view for explaining the steps of manufacturing absorbent articles according to an embodiment.

Next, one example of a method for manufacturing absorbent articles, according to the embodiment, will be described with reference to FIG. 2. FIG. 2 is a view for explaining the method for manufacturing absorbent articles, and shows a part of a course in which absorbent articles are manufactured. FIG. 2 shows a direction of conveying constituent elements in the course of manufacture as a conveyance direction MD, and shows a direction perpendicular to the conveyance direction as a cross direction CD. The method for manufacturing absorbent articles is to manufacture the absorbent articles 1 in a state in which the articles are continuous in the widthwise direction.

It is to be noted that in respect of a method that is not described in the embodiment, an existing method can be employed. In addition, the manufacturing method described hereinafter is provided as a mere example, and manufacturing by another manufacturing method is also possible.

The method for manufacturing absorbent articles includes at least an absorbent main body forming step S1, an exterior body forming step S2, a leg hole opening forming step S3, a constituent element joining step S4, a folding step S5, a joining step S6, and a cutting step S7.

In the absorbent main body forming step S1, the absorbent main body 1A is formed. Specifically, an absorption material is laminated to thereby mold the absorber 40, the absorber 40 is disposed on a continuous web constituting the topsheet 10, or a leakage preventing unit is formed.

The exterior body forming step S2 is constituted so that an exterior body 1B is formed. In the embodiment, this step is constituted so that a foreside continuum 75F in which an exterior sheet disposed at an belly-side of a wearer is continuous and a backside continuum 75R in which an exterior sheet disposed at a backside of the wearer is continuous are separately formed, and the foreside continuum 75F and the backside continuum 75R are coupled to each other via an intermediate exterior sheet so as to manufacture an exterior body 1B.

Specifically, between a web constituting the a foreside exterior topsheet 70F and a web constituting a foreside exterior backsheet 80F, a hipline elastic member 3A and a front leg-line elastic member 5F are disposed to thereby form a foreside continuum 75F, and between a web constituting a backside exterior topsheet 70R and a web constituting a backside exterior backsheet 80R, an hipline elastic member 3A and a back leg-line elastic member 5R are disposed to thereby form a backside continuum 75R.

Next, after an unnecessary portion of a front leg-line elastic member 5F and a back leg-line elastic member 5R (a portion deviating from the foreside continuum 75F and the backside continuum 75R) has been cut, the foreside continuum 75F and the backside continuum 75R are joined with each other by the intermediate exterior sheet 85. In this manner, an exterior continuum 90 in which exterior bodies 1B of individual products are continuous in the widthwise direction is formed.

The leg hole opening forming step S3 is to cut the exterior body 1B along a leg hole opening forming unit. In this manner, a leg hole opening unit disposed on a leg of a wearer is formed.

The constituent element joining step S4 is a workpiece disposition step, and the absorbent main body 1A as a workpiece which is a constituent element constituting a part of the absorbent article is disposed on a sheet-shaped continuous web to be continuously conveyed by a rotary drum at which a suction unit sucking a workpiece is provided and on a web (continuum) on which an elastic member is disposed that is expanded in a conveyance direction of the web and in a cross direction crossing the conveyance direction, and the exterior body 1B and the absorbent main body 1A are joined with each other.

The workpiece disposition step includes: a workpiece rotation step of sucking a workpiece at a workpiece reception point at which a rotary drum receives the workpiece and then converting a disposition direction of the workpiece from a first disposition direction of the workpiece at the reception point to a second disposition direction of the workpiece at a delivery point of the workpiece onto a web; and a workpiece delivery step of, at the delivery point, delivering the workpiece sucked by the suction unit onto the web.

Specifically, the absorbent main body 1A is disposed on a continuum of the exterior body 1B on which a leg hole opening unit is formed, and the absorbent main body 1A and the exterior body 1B are joined with each other via an adhesive.

In addition, a method for manufacturing absorbent articles, according to the embodiment, has: a first guiding step of at a delivery point, disposing a web so that an outer edge portion of a workpiece and a web come into contact with each other; and a second guiding step of at an abutment point on an upstream side in a conveyance direction more significantly than the delivery point, disposing a web so that the outer edge portion of the workpiece is spaced from the web and a central portion of the workpiece and the web come into contact with each other.

In the folding step S5, the continuum of the absorbent article in which the absorbent main body 1A and the exterior body 1B are joined with each other is folded with reference to a fold including a center in a cross direction and taken along a conveyance direction.

In the joining step S6, end portions in a widthwise direction of the folded absorbent article are joined with each other. Specifically, a front waistline edge portion 4 and a back waistline edge portion 6 are joined with each other, and a front waistline edge portion 4' and a back waistline edge portion 6' are joined with each other.

In the cutting step S7, the continuum of the absorbent article is cut in size of one product along a longitudinal direction (cross direction) of the absorbent article. In this manner, an absorbent article 1 is manufactured.

(3) Structure of Apparatus for Manufacturing Absorbent Articles

Figure 3:
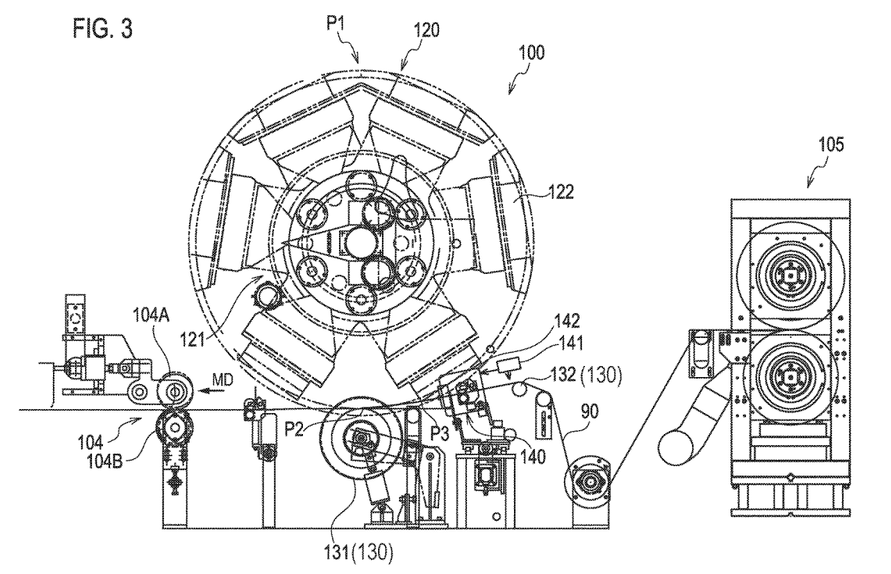
FIG. 3 is a perspective view showing an apparatus for manufacturing absorbent articles, according to an embodiment.
Figure 4:
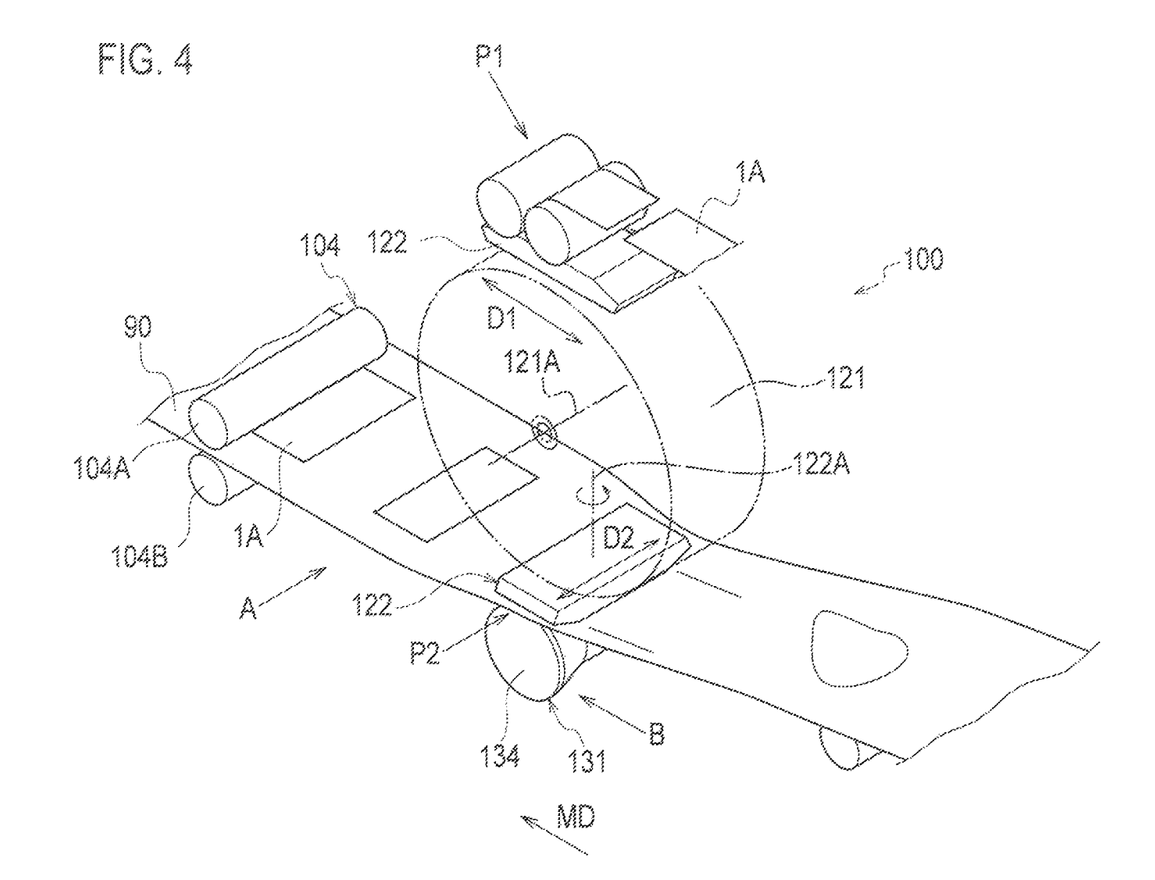
FIG. 4 is a side view showing the apparatus for manufacturing absorbent articles according to an embodiment.
Figure 5:
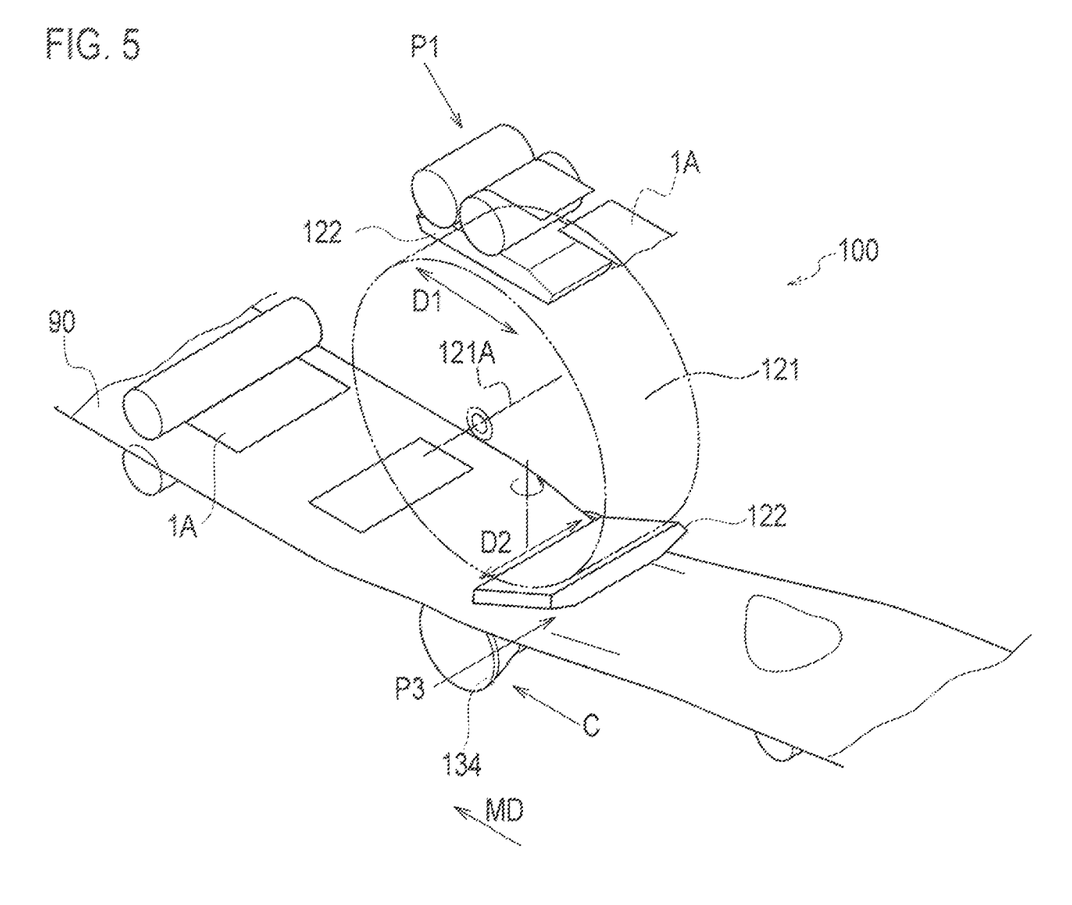
FIG. 5 is a side view showing the apparatus for manufacturing absorbent articles according to an embodiment.
Figure 6:
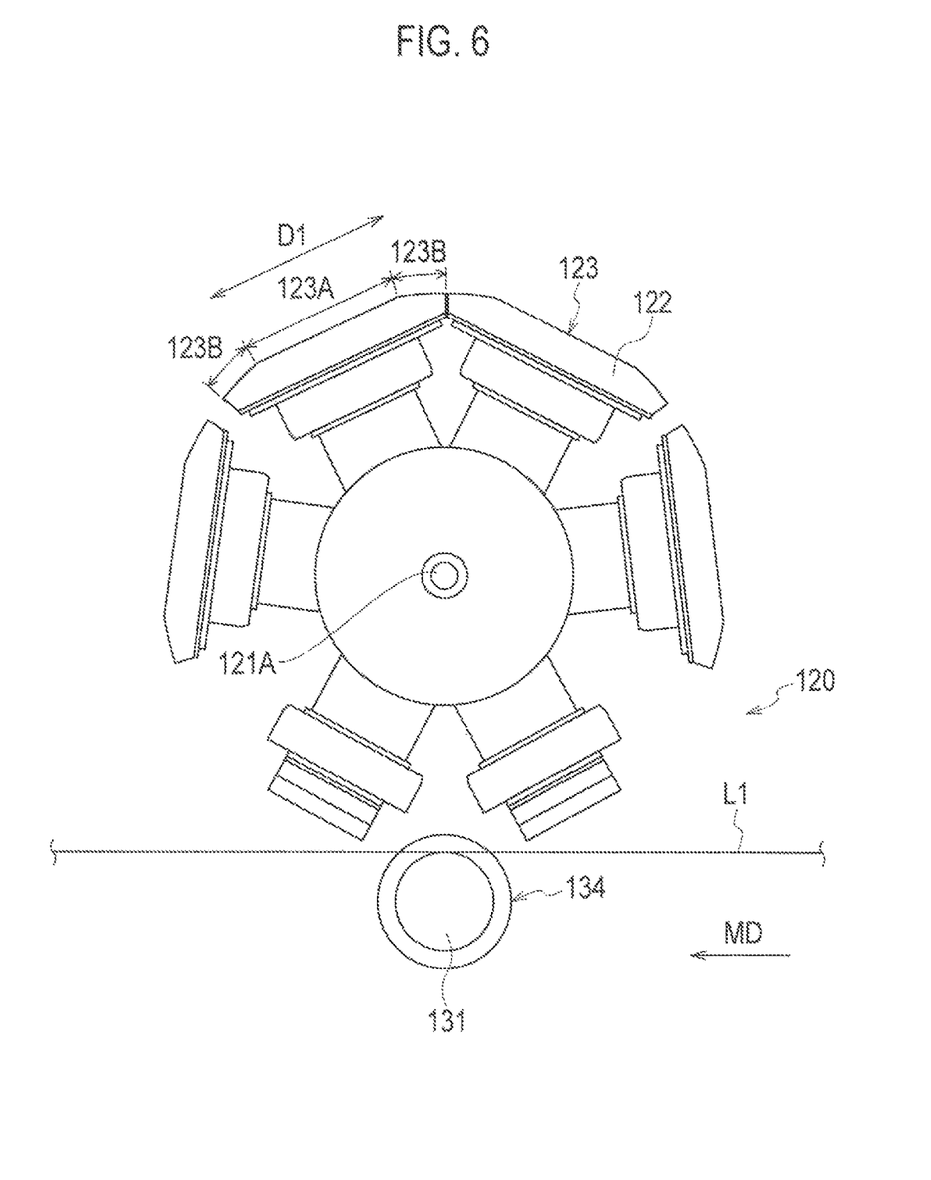
FIG. 6 is a front view of a rotary drum as indicated by the arrow A shown in FIG. 4.
Figure 7:
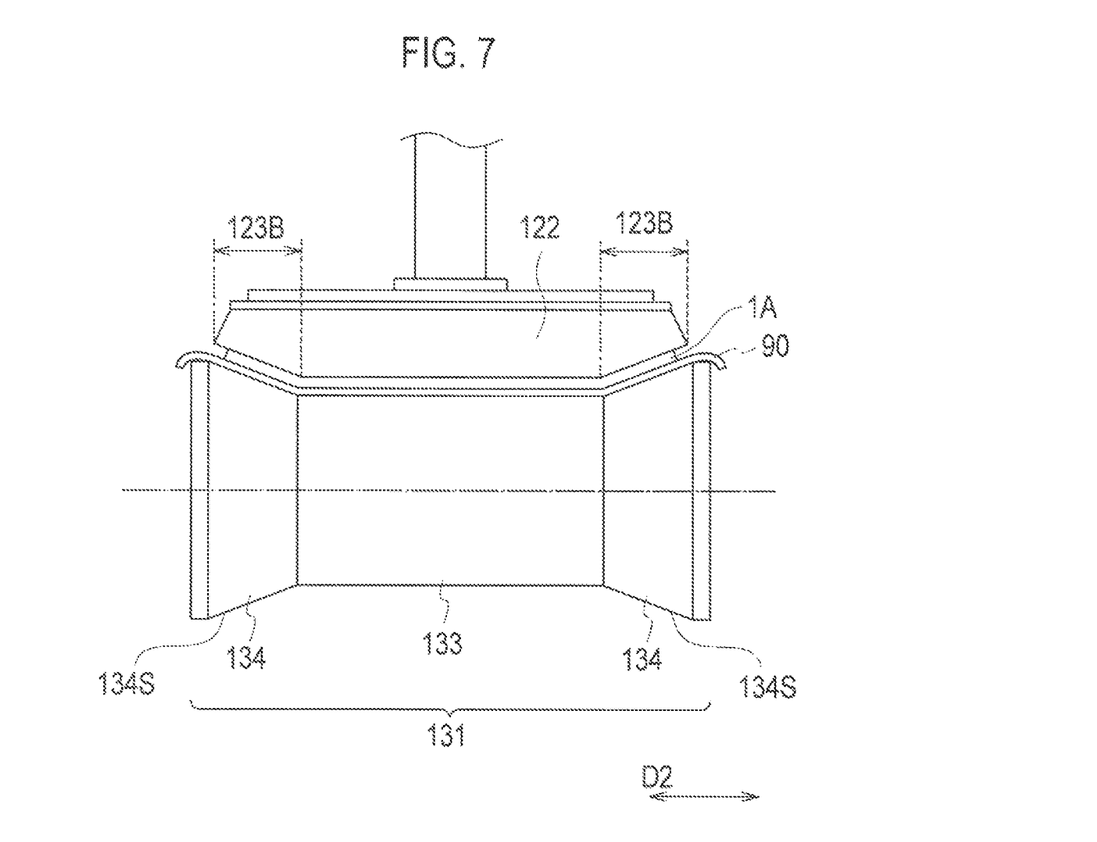
FIG. 7 is a side view of a workpiece at a point of receipt as indicated by the arrow B shown in FIG. 4.
Figure 8:
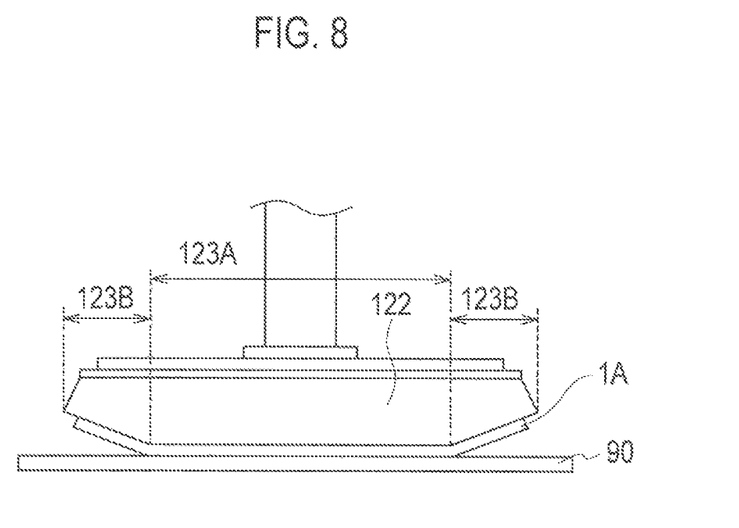
FIG. 8 is a side view of a workpiece at a point of abutment as indicated by the arrow C shown in FIG. 5.
Figure 9:
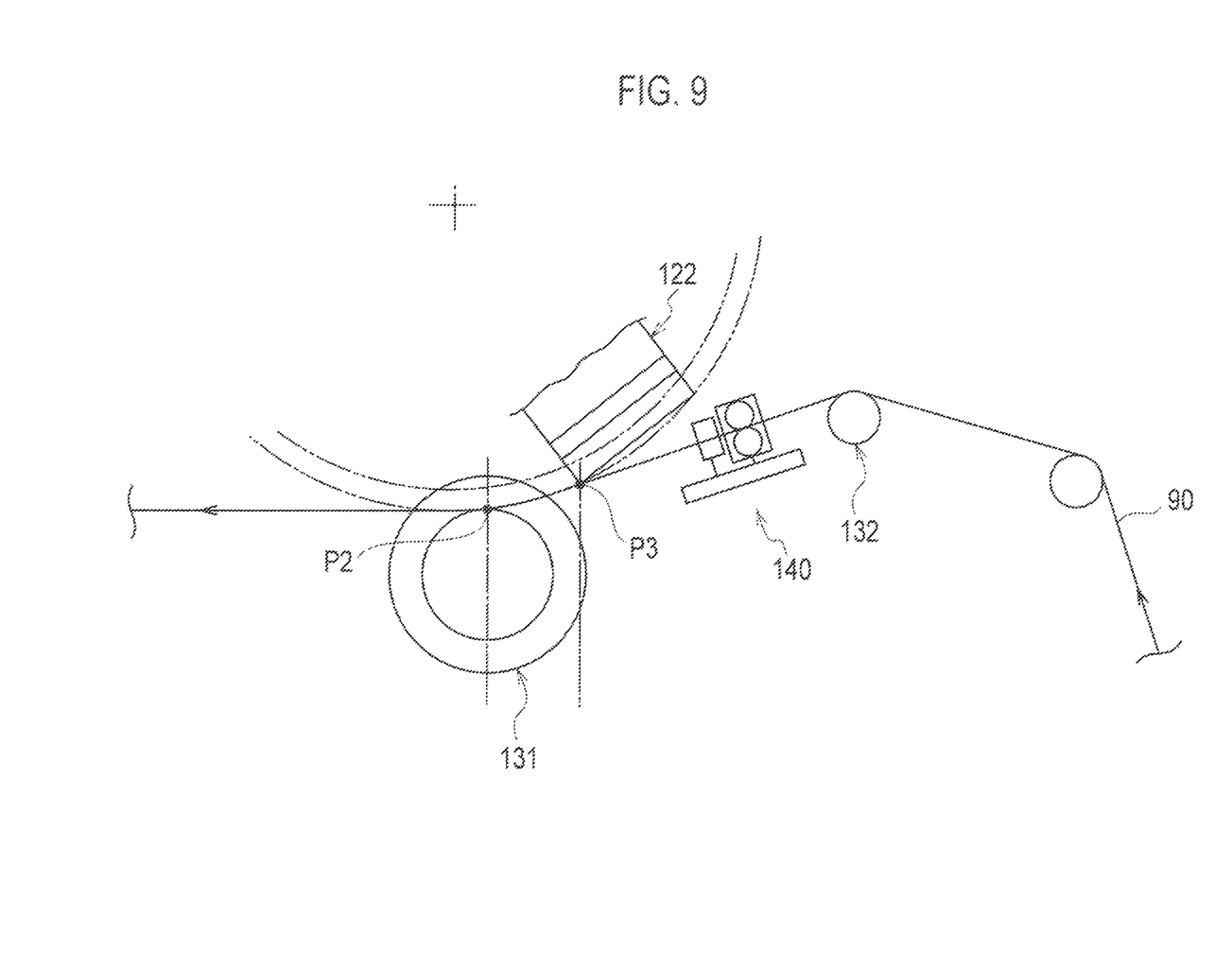
FIG. 9 is a view schematically showing a positional relationship of a web between a delivery point P2 and an abutment point P3.

Next, an entire structure of an apparatus for manufacturing absorbent articles to be used in the constituent element joining step S4 mentioned above will be described with the drawings. FIG. 3 is a front view showing an entire structure of an apparatus for manufacturing absorbent articles, according to the embodiment. FIG. 4 and FIG. 5 are perspective views showing the apparatus for manufacturing absorbent articles, according to the embodiment, and FIG. 6 is a front view of a rotary drum as indicated by the arrow A shown in FIG. 4. FIG. 7 is a side view of a workpiece as indicated by the arrow B shown in FIG. 4, and FIG. 8 is a side view of a workpiece as indicated by the arrow C shown in FIG. 5. FIG. 9 is a view schematically showing a positional relationship of a web at a delivery point P2 and an abutment point P3.

An absorbent article manufacturing apparatus 100 is constituted so as to rotate a workpiece constituting the absorbent main body 1A at an angle of 90 degrees and then dispose this workpiece on a continuum as a web constituting the exterior body 1B.

The absorbent article manufacturing apparatus 100 has a workpiece disposition mechanism 120, a web position guiding mechanism 130, and a web position adjustment mechanism 140.

To the absorbent article manufacturing apparatus 100, a continuum 90 is supplied from the right side shown in FIG. 4, and the absorbent main body 1A is supplied from the upper side shown in FIG. 4. With the continuum 90, a foreside continuum 75F, a backside continuum 75R, and an intermediate exterior sheet 85 are joined with each other, and at the continuum 90, a leg hole opening unit is formed by a cutting mechanism 105 disposed on an upstream side of the absorbent article manufacturing apparatus 100.

The workpiece disposition mechanism 120 is provided with a rotary drum 121 and a plurality of suction units (hereinafter, referred to as suction pads 122) that are provided on an outer periphery of the rotary drum 121. The workpiece disposition mechanism 120 receives a workpiece on a suction pad 122 at the reception point P1, rotates the suction pad 122 around a rotary shaft 122A along a radial direction of the rotary drum while conveying the workpiece along a circumferential direction of the rotary drum with rotation of the rotary drum, and changes a direction of the workpiece. Further, the workpiece of which a direction is changed is disposed on a web and then the workpiece and the web are joined with each other.

The web position guiding mechanism 130 is provided with: a first guide unit 131, which is provided at an opposite side to a rotary drum via a web, and a second guide unit 132. The web position guiding mechanism 130 guides a position of the web at the delivery point P2 at which the workpiece is delivered onto the web and at the abutment point P3 on the upstream side in the conveyance direction more significantly than the delivery point P2. A first guiding step is executed by the first guide unit 131, and a second guiding step is executing by the second guide unit 132.

The web position adjustment mechanism 140 detects a position of an end portion in a cross direction of the continuum 90, and based on the position information, adjusts a position in a cross direction of a web.

Next, constituent elements constituting the absorbent article manufacturing apparatus 100 will be described in detail. Specifically, a description will be given with respect to (3.1) Workpiece Disposition Mechanism, (3.2) Web Position Guiding Mechanism, and (3.3) Web Position Adjustment Mechanism.

(3.1) Workpiece Disposition Mechanism

The rotary drum 121 constituting the workpiece disposition mechanism 120 has the suction pad 122 for sucking a workpiece that is a constituent element constituting a part of the absorbent article 1. The rotary drum 121 rotates around the rotary shaft 121A to thereby dispose the workpiece (the absorbent main body 1A in the embodiment) that is sucked by the suction pad 122, on the continuum 90 to which the constituent elements of the absorbent article is to be conveyed in a continuous state.

The rotary drum 121 has a rotational mechanism in the rotary drum 121. Specifically, the rotary drum 121 rotates the suction pad 122 at an angle of 90 degrees by the rotational mechanism while conveying the suction pad 122 upward of the continuum 90.

The suction pad 122 constituting the workpiece disposition mechanism sucks the absorbent main body 1A on a one-by-one pieces basis. By the rotary drum 121, the suction pad 122 is conveyed upward of the continuum 90 in which the exterior body 1B disposed outside more significantly than the absorbent main body 1A is continuous.

The suction pad 122 sucks the absorbent main body 1A and rotates the rotary drum 121, and in this duration, change a disposition direction at the reception point P1 of the absorbent main body 1A to a disposition direction at the delivery point P2 of the absorbent main body 1A by the rotational mechanism provided in the rotary drum 121. The delivery point P2 lies immediately under a rotary shaft 121A of the rotary drum 121.

As shown in FIG. 4, in a cross section taken along a first disposition direction D1 of the suction pad 122 at the reception point P1, a central portion 123A of the suction face 123 of the suction pad 122 is disposed proximally from the rotary shaft 121A of the rotary drum 121 more significantly an outer edge portion (an end portion 123B) lying outside of the central portion 123A of the suction face 123.

As shown in FIG. 4, with respect to the shape of the suction face 123 of the suction pad 122 at the delivery point P2, the outer edge portion (end portion 123B) in a second disposition direction D2 of the suction face 123 is inclined toward the rotary shaft 121A side of the rotary drum 121. Specifically, in a viewpoint from an extension direction of the rotary shaft 121A of the rotary drum 121 at the delivery point P2, the end portion 123B in the second disposition direction D2 of the suction face 123 is inclined to the rotary shaft 121A side in comparison with the central portion 123A.

The suction pad 122 at the delivery point P2 is that in comparison with the central portion 123A of the suction face 123, the outer edge portion (end portion 123B) of the suction face 123 close to the rotary shaft 121A side of the rotary drum 121. In addition, a thickness of the absorbent main body 1A of the embodiment is different in a region in which an absorber is disposed and a region in which the absorber is not disposed, and the region in which the absorber is disposed is thicker. In addition, in a cross section taken along the second disposition direction D2 of the suction pad 122 at the delivery point P2, an external shape of a workpiece sucked by the suction pad 122 is that in comparison with the central portion of the workpiece, the outer edge portion lying outside of the central portion of the workpiece is close to the rotary shaft 121A side of the rotary drum 121. In the region in which the absorber of the absorbent main body 1A is not disposed lies at the outer edge portion, and is disposed so as to be close to the rotary shaft 121A side of the rotary drum 121 in accordance with an external shape of the suction pad 122.

It is to be noted that as in the embodiment, a workpiece may be constituted so that a thickness of the outer edge portion is small in comparison with that of a central portion or the like or a thickness of the workpiece may be uniform as a whole.

(3.2) Web Position Guiding Mechanism

The web position guiding mechanism 130 guides a position of the continuum 90. The web position guiding mechanism is provided with: the first guide unit 131 that disposes a web so as to abut the outer edge portion of a workpiece and the web against each other at the reception point P2; and the second guide unit 132 that lies on the upstream side in the conveyance direction more significantly than the reception point, and disposes a web so as to abut the central portion of the workpiece and the web. FIG. 4 an FIG. 7 show a state in which the suction pad 122 lies at the delivery point P2, and FIG. 5 and FIG. 8 show a state in which the suction pad 122 lies at the abutment point P3.

The first guide unit 131 disposes the outer edge portion of the continuum 90 that is a portion corresponding to the outer edge portion of the absorbent main body 1A at the delivery point P2, on the rotary shaft 121A side of the rotary drum 121 more significantly than the central portion in the widthwise direction of the continuum 90. Namely, in the embodiment, the first guide unit 131 disposes the outer edge portion of the continuum 90 in the widthwise direction of the continuum 90, on the suction pad 122 side more significantly than the central portion in the widthwise direction of the continuum 90.

The second guide unit 132 guides the continuum 90 so that the end portion in the cross direction and the central portion in the cross direction, of the continuum 90, are established in a substantially horizontal state. The second guide unit 132 is disposed on the upstream side in the conveyance direction more significantly than the web position adjustment mechanism 140, and adjusts a conveyance passageway of the web in a vertical direction. A conveyance face of the web of the second guide unit 132 lies more upward than the delivery point P2. Therefore, the conveyance passageway of the web on the upstream side in the conveyance direction more significantly than the delivery point P2 lies upward as it goes to the upstream in the conveyance direction, and approaches to the outer circumferential face side of the rotary drum 121. Accordingly, the abutment point P3 lies more upward than the delivery point P2.

At the abutment point P3, the continuum 90 is in the horizontal state in the cross direction, and the central portion of the workpiece lies outside (web side) in the radial direction of a rotary body more significantly than the outer edge portion of the continuum 90. Therefore, at the abutment point, the central portion of the workpiece and the continuum 90 abut against each other, and the outer edge portion of the workpiece and the continuum 90 are spaced from each other.

It is to be noted that the outer edge portion of the continuum 90, at the delivery point P2 and the abutment point P3, denotes a region lying outside more significantly than the central portion of the continuum 90 in the widthwise direction of the continuum 90. In the embodiment, the outer edge portion of the absorbent main body 1A is a portion corresponding to the outer edge portion (end portion 123B) of the suction pad 122 at the delivery point P2, and an end portion in the longitudinal direction of the absorbent main body 1A in the longitudinal direction of the absorbent article.

The outer edge portion in the widthwise direction of the continuum 90, at the delivery point P2, does not always denote the end portion in the widthwise direction of the continuum 90. For example, the continuum 90 means that in the case where it is further wide in the widthwise direction, the end portion in the widthwise direction of the continuum 90 may be more distant from the suction pad 122 than the central portion in the widthwise direction of the continuum 90.

A detailed view of a structure of the first guide unit 131 will be described in detail with reference to FIG. 7. The first guide unit 131 is a roller mechanism that is rotatable along the conveyance direction MD of the continuum 90. The first guide unit 131 is made of a central roller 133 and an outside roller 134 that is disposed at each side in the cross direction of the central roller 133. The central roller 133 is provided at a position corresponding to the central portion 123A of the suction pad in a state in which the suction pad 122 is taken along the second disposition direction D2. The outside roller 134 is provided at a position corresponding to the end portion 123B of the suction pad 122 in a state in which the suction pad 122 is taken along the second disposition direction D2. Two outside rollers 134 are provided outward in the widthwise direction of the continuum 90 of the central roller 133.

It is noted that in the following description, two outside rollers 134 both have similar features and thus only one outside roller will be described, and a duplicate description of the other outside roller is not given.

Rollers employed in the first guide unit 131 are formed of an elastic member. Specifically, the rollers employed in the first guide unit 131 are formed of a rubber, a urethane rubber, or a silicon rubber or the like formed in a sponge shape of silicon or urethane or the like.

The first guide unit 131 is provided on the downstream side in the conveyance direction MD of the continuum 90 more significantly than the abutment point P3. An outer circumferential portion of the first guide unit 131 is provided on the rotary shaft 121A side of the rotary drum 121 more significantly than the tangential line L1 of a rotational trajectory at a center of the suction face 123 at the delivery point P2 in a viewpoint from the extension direction of the rotary shaft 121A of the rotary drum 121.

In a viewpoint from the conveyance direction MD of the continuum 90, an outer circumferential face 134S of the outside roller 134 is substantially parallel to the line taken along the outer edge portion (end portion 123B) of the suction face 123. The outside roller 134 increases in outer diameter as it goes outward in the widthwise direction of the continuum 90. A surface of the outside roller 134 may include slight irregularities.

(3.3) Web Position Adjustment Mechanism

The web position adjustment mechanism adjusts a position in a cross direction of a web on the downstream side in the conveyance direction more significantly than the cutting mechanism 105 and on the upstream side in the conveyance direction more significantly than the abutment point P3.

The web position adjustment mechanism 140, as shown in FIG. 3, has: a sensor 141 that outputs positional information in a cross direction of each detection target portion set on a web; and an adjustment mechanism 142 that adjusts a position in a cross direction of a web, based on the positional information.

The continuum 90 has one pair of a side edge and a second side edge opposed to each other in the cross direction CD and extending in parallel in the conveyance direction MD. The adjustment mechanism 142 is a control means relative to the continuum 90 for guiding at least one of proximity of a first side edge and proximity of the second side edge up to a predetermined position in the cross direction CD and then adjusting the continuum 90 in a required width. The sensor 141 and the adjustment mechanism 142 can employ a variety of structures, and for example, a sensor and an adjustment mechanism disclosed in Japanese Unexamined Patent Application Publication No. 2004-262556 can be employed.

Positional adjustment of the continuum 90 is performed on the upstream side in the conveyance direction more significantly than the abutment point P3 between the absorbent main body and the continuum 90, whereby even in the case the continuum is partially contracted by an elastic member. When a position in the cross direction is shifted, a shift in position of the continuum can be speedily corrected. As a result, the continuum is conveyed at a precise position, the absorbent main body can be joined at a correct position of the continuum, and a positional shift between the continuum and the absorbent main body 1A can be prevented.

(4) Operation of Apparatus for Manufacturing Absorbent Articles

Next, an operation of an apparatus for manufacturing absorbent articles, according to the embodiment (hereinafter, referred to as "absorbent article manufacturing apparatus 100") will be described.

The absorbent main body 1A is supplied from an upward side of the absorbent article manufacturing apparatus 100.

In the absorbent main body 1A formed as a continuous band-shaped body, the longitudinal direction of the absorbent main body 1A is taken along the longitudinal direction of the band-shaped body, namely in the conveyance direction of the band-shaped body.

The suction pad 122 sucks the absorbent main body 1A at the reception point P1 of the absorbent main body 1A.

The rotary drum 121 rotates the suction pad 122 at an angle of 90 degrees while conveying the suction pad 122 upward of the continuum 90. Specifically, the rotary drum 121 rotates the suction pad 122 at an angle of substantially 90 degrees by a rotational mechanism that is provided in the rotary drum 121 while conveying the suction pad 122 from the reception point P1 to the delivery point P2 of the absorbent main body 1A.

In this manner, the suction pad 122 changes the disposition direction of the absorbent main body 1A from the first disposition direction D1 of the absorbent main body 1A to the second disposition direction D2 of the absorbent main body 1A.

In addition, the absorbent main body 1A to be conveyed in a state in which it is sucked by the suction pad 122 abuts the continuum 90 to which an adhesive is applied, at the abutment point P3 lying on the upstream side in the conveyance direction more significantly than the reception point P2. The abutment point P3 is a point at which the absorbent main body 1A as a workpiece and the continuum 90 constituting the exterior body 1B first abut against each other. In the embodiment, in comparison with the central portion of the absorbent main body 1A, the outer edge portion of the absorbent main body 1A is close to the rotary shaft side of the rotary drum. Therefore, the central portion of the absorbent main body 1A corresponding to the central portion of the suction face 123 abuts against the continuum 90 more earlier than the outer edge portion of the absorbent main body 1A. The abutment point P3 is a point at which the central portion of the absorbent main body 1A and the continuum 90 abut against each other.

Afterwards, a workpiece is conveyed in a state in which the workpiece is sucked by the suction pad from the abutment point P3 to the delivery point P2. The suction pad 122 releases suction of the absorbent main body 1A and then releases the absorbent main body 1A at the delivery point P2 of the absorbent main body 1A.

The first guide unit 131 positions the continuum 90 on the suction pad 122 side at the delivery point P2. Specifically, the first guide unit 131 disposes the outer edge portion in the widthwise direction of the continuum 90 (the continuum 90 corresponding to the outer circumferential face 134S of the outside roller) on the rotary shaft side of the rotary drum 121 more significantly than the central portion in the widthwise direction of the continuum 90, and positions the continuum 90.

In this manner, the absorbent main body 1A is disposed on the continuum 90 that is conveyed.

Further, the pressing mechanism 104 is provided on the downstream side in the conveyance direction more significantly than the delivery point P2. The pressing mechanism 104 is provided one pair of upper roller 104A and lower roller 104B that are disposed so as to be opposed to each other via the continuum 90, and compresses a member passing between these rollers in a thickness direction. The continuum 90 and the absorbent main body 1A that is joined on the continuum 90 are pressed and brought into intimate contact with each other in the thickness direction by the pressing mechanism 104.

(5) Functions and Advantageous Effects

As described above, according to the embodiment, on the upstream side in the conveyance direction more significantly than the delivery point P2, the continuum 90 in a horizontal state abuts against the absorbent main body 1A. Therefore, the central portion of the absorbent main body 1A comes into contact with the continuum 90 more earlier than the outer edge portion of the absorbent main body 1A and then the outer edge portion of the absorbent main body 1A and the continuum 90 all are in abutment against each other. After that, the outer edge portion of the continuum 90 is pushed up by the first guide unit 131, and in the downstream side in the conveyance direction more significantly than the abutment point P3, the outer edge portion of the absorbent main body 1A and the continuum 90 come into contact with each other, and the central portion of the absorbent main body 1A and the continuum 90 come into contact with each other.

The continuum 90 is thus conveyed, whereby the absorbent main body 1A gradually comes into contact with a web from the central portion toward the outer edge portion. Therefore, while a wrinkle between the continuum 90 and the absorbent main body 1A is released from the central portion to the outer edge portion, the absorbent main body 1A is disposed on the continuum 90, and these bodies can be joined with each other.

Further, the central portion of the absorbent main body 1A and the central portion of the continuum 90 are positioned, and are positioned from the positioned center toward the outer edge portion on both ends. An elastic member is disposed in a wavy shape on the continuum 90, thereby even in the case where a contracted state of the continuum 90 is not uniform, a positional shift between the continuum 90 and the absorbent main body 1A can be restrained.

In addition, the outside roller 134 of the first guide unit 131 has the outer circumferential face 134S to be provided at a position corresponding to the end portion 123B of the suction pad 122. Namely, the first guide unit 131 becomes further close to the central portion and the shape of the outer edge portion of the absorbent main body 1A, and the continuum 90 can be positioned and thus the continuum 90 can be further rigidly adhered to the absorbent main body 1A.

The first guide unit 131 further includes the central roller 133 provided at a position corresponding to the central portion of the suction pad 122, and thus the continuum 90 can be positioned in accordance with the shapes of the central portion and the outer edge portion of the absorbent main body 1A. Therefore, the continuum 90 can be further rigidly adhered to the absorbent main body 1A.

The rollers employed in the first guide unit 131 are formed of an elastic member and thus can be deformed when the continuum 90, in accordance with the shape of the absorbent main body 1A. In this manner, applying a redundant stress or the like to the continuum 90 can be restrained. In addition, an outer diameter of the outside roller 134 increases as it goes to the outside in the widthwise direction of the continuum 90 and thus a difference in circumferential speed (so called circumferential difference) occurs with the outside roller 134 in accordance with the outer diameter. On the other hand, according to the rollers formed of the elastic member, a difference in circumferential speed at the time of transfer can be mitigated due to a deformation of the elastic member and thus the first guide unit 131 can further restrain an occurrence of a wrinkle or a transfer failure.

In addition, if the continuum and the absorbent main body 1A are conveyed in a state in which the absorbent main body 1A disposed on the continuum is not securely adhered, there is an apprehension that the position of the absorbent main body 1A may be shifted. However, the continuum 90 and the absorbent main body 1A are pressed by the pressing mechanism 104 and thus the absorbent main body 1A is securely adhered onto the continuum, and a positional shift can be restrained.

Further, on the upstream side in the conveyance direction more significantly than the abutment point P3 between the absorbent main body and the continuum 90, positional adjustment of the continuum 90 is performed. Therefore the continuum is partially contracted by the elastic member, and even if the position in the cross direction is shifted, a change in position of the continuum can be speedily corrected. As a result, the continuum is conveyed at a precise position, the absorbent main body can be joined at a correct position of the continuum, and a positional shift between the continuum and the absorbent main body 1A can be prevented.

(6) Other Embodiments

As described above, while the contents of the present were disclosed through the embodiment of the present invention, it should not be understood that a discussion and drawings forming a part of this disclosure limit the present invention. From this disclosure, a variety of substitutive embodiments, examples, and operational techniques would have been self-evident to one skilled in the art.

While, in the embodiment, the first guide unit 131 is provided with the central roller 133 and the outside roller 134, the manufacturing apparatus according to the present invention is not limitative to this structure. For example, the first guide unit 131 may dispose a web so as to abut at least an outer edge portion of a web and an outer edge portion of a workpiece against each other, or alternatively may be made of only an outside roll.

In addition, while the apparatus for manufacturing absorbent articles, according to the embodiment, is provided with the web position adjustment mechanism, the apparatus for manufacturing absorbent articles, according to the present invention, does not always need to be provided with the web position adjustment mechanism.

Further, the web position adjustment mechanism is not limitative to the configuration of the embodiment, and a variety of configurations can be employed. For example, the web position adjustment mechanism is provided with: an image photographing means for photographing each detection target portion set on the web on which such each detection target portion is to be photographed; and a sensor to output positional information in the cross direction of such each detection target portion, based on image data photographed by the photographing means, and the adjustment mechanism may be constituted so as to adjust the position in the cross direction of the web, based on the positional information.

Moreover, while, in the embodiment, the above adjustment mechanism is constituted so as to detect positions of the first side edge and the second side edge that are end portions in the cross direction of the continuum 90 and then adjust the position of the web, this mechanism may be constituted so as to adjust a position of another portion of the absorbent article and then adjust the position of the web.

For example, the web position adjustment mechanism may be constituted so as to adjust the position in the cross direction of the web, based on positional information of the leg hole opening unit of the exterior body. The leg hole opening unit elastic member is disposed in proximity to the leg hole opening unit, and the position of the web may be shifted due to contraction of the elastic member. However, the position of the web is adjusted based on the positional information of the leg hole opening unit, whereby the positional shift of the leg hole opening unit is speedily adjusted, and the positional shifts of the absorbent main body 1A and the exterior body 1B can be prevented.

In addition, the web position adjustment mechanism may be constituted so as to adjust the position in the cross direction of the web, based on positional information of a cross point at which the leg hole opening unit and the end portion in the widthwise direction of the absorbent main body cross each other. The cross point at which the leg hole opening unit and the end portion in the widthwise direction of the absorbent main body cross each other at which the leg hole opening unit and the end portion in the widthwise direction of the absorbent main body cross each other is a portion corresponding to a groin region of a wearer and a portion which should come into intimate contact with a body. If a positional relationship between the exterior body and the absorbent main body 1A at the portion is not appropriate, the absorbent main body 1A is lifted with respect to the exterior body, and there is an apprehension that the absorbent article may not fit to a body. However, the position of the web is adjusted based on positional information of the cross point at which the leg hole opening unit and the end portion in the widthwise direction of the absorbent main body cross each other, whereby a positional relationship between the absorbent main body 1A and the exterior body 1B at a portion to be applied to the groin region can be adjusted, and a feeling of fitting in the groin region can be improved.

Further, while the first guide unit according to the embodiment is characterized in that the central roller 133 specifying the position of the central portion in the cross direction and the outside roller 134 specifying the position of the end portion in the cross direction are integrated with each other, for example, the central roller 133 and the outside roller 144 are structured so as to be separated from each other, the central roller is disposed on the upstream side in the conveyance direction, the outside roller is disposed on the downstream side in the conveyance direction, the central portion of the web is pressed against the workpiece side, and thereafter, the outside edge portion may be pressed against the workpiece side.

Thus, it is a matter of course that the present invention includes a variety of embodiments or the like that are not described herein. Therefore, a technical scope of the present invention is defined by only the specific matters of the invention associated with the scope of claims reasonable from the foregoing description.

The entire contents of Japanese Patent Application No. 2012-124896 (filed on May 31, 2012) is incorporated in the present specification by reference.

INDUSTRIAL APPLICABILITY

It is possible to provide an apparatus for manufacturing absorbent articles and a method for manufacturing absorbent articles which are capable of transferring a workpiece while restraining an occurrence of a wrinkle or a twist in the case of adhering a workpiece such as an absorbent main body on a web to be continuously conveyed.

The invention claimed is:

1. A method of manufacturing absorbent articles, said method comprising:
a workpiece disposition step of disposing a workpiece, which is a constituent element constituting a part of an absorbent article, by a rotary drum having a suction unit sucking the workpiece on a sheet-shaped continuous web on which an elastic member expanded in a conveyance direction of the web and in a cross direction crossing the conveyance direction is disposed, wherein the workpiece disposition step includes:
a workpiece rotation step of (i) sucking the workpiece at a reception point where the workpiece is received by the rotary drum, and (ii) rotating the workpiece from a first disposition direction of the workpiece at the reception point to a second disposition direction of the workpiece at a delivery point where the workpiece is to be delivered onto the web, wherein, in a cross section taken along the second disposition direction at the delivery point, an outer edge portion of the workpiece sucked by the suction unit is closer to the rotary drum than a central portion of the workpiece;
a workpiece delivery step of delivering, onto the web, the workpiece sucked by the suction unit at the delivery point;
a first guiding step of disposing the web to contact with the outer edge portion of the workpiece at the delivery point; and
a second guiding step of disposing the web to be spaced from the outer edge portion of the workpiece and to contact with the central portion of the workpiece, at an abutment point on an upstream side of the delivery point in the conveyance direction; and
a web position adjustment step of adjusting a position of the web in the cross direction on an upstream side of the abutment point in the conveyance direction, wherein the web position adjustment step includes:
detecting a positional information of a detection target portion set in the cross direction on the web, said detection target portion including an end portion of the web in the cross direction; and
adjusting a position of the web in the cross direction based on the positional information of the end portion of the web in the cross direction,
wherein the web position adjustment step further includes:
photographing the detection target portion set on the web;
outputting the positional information of the detection target portion in the cross direction based on image data obtained by said photographing, and
the position of the web in the cross direction is adjusted based on the outputted positional information.

2. The method according to claim 1, wherein the first guiding step includes disposing the web at the delivery point to contact with the outer edge portion of the workpiece and the central portion of the workpiece.

3. The method according to claim 1, further comprising a step of pressing the web and the workpiece between an upper roll and a lower roll at a downstream side of the delivery point in the conveyance direction of the web.

4. The method according to claim 1, wherein the absorbent article has:
an exterior body including
a front waistline region configured to be disposed on a belly-side of a wearer,
a back waistline region configured to be disposed on a back side of the wearer, and
leg hole opening units each configured to be disposed along a leg of the wearer; and
an absorbent main body disposed on a skin contact surface side of the exterior body and including an absorber, and
in the workpiece disposition step, the workpiece as the absorbent main body is disposed onto a section of the web, said section defining the exterior body.

5. The method according to claim 1, further comprising:
a step of adjusting a conveyance passageway of the web in a vertical direction by a guide unit before the web position adjustment step.

6. A method of manufacturing absorbent articles, said method comprising:
a workpiece disposition step of disposing a workpiece, which is a constituent element constituting a part of an absorbent article, by a rotary drum having a suction unit sucking the workpiece on a sheet-shaped continuous web on which an elastic member expanded in a conveyance direction of the web and in a cross direction crossing the conveyance direction is disposed, wherein the workpiece disposition step includes:
a workpiece rotation step of (i) sucking the workpiece at a reception point where the workpiece is received by the rotary drum, and (ii) rotating the workpiece from a first disposition direction of the workpiece at the reception point to a second disposition direction of the workpiece at a delivery point where the workpiece is to be delivered onto the web, wherein, in a cross section taken along the second disposition direction at the delivery point, an outer edge portion of the workpiece sucked by the suction unit is closer to the rotary drum than a central portion of the workpiece;
a workpiece delivery step of delivering, onto the web, the workpiece sucked by the suction unit at the delivery point;
a first guiding step of disposing the web to contact with the outer edge portion of the workpiece at the delivery point; and
a second guiding step of disposing the web to be spaced from the outer edge portion of the workpiece and to contact with the central portion of the workpiece, at an abutment point on an upstream side of the delivery point in the conveyance direction; and
a web position adjustment step of adjusting a position of the web in the cross direction on an upstream side of the abutment point in the conveyance direction, wherein the web position adjustment step includes:
detecting a positional information of a detection target portion set in the cross direction on the web, said detection target portion including an end portion of the web in the cross direction; and
adjusting a position of the web in the cross direction based on the positional information of the end portion of the web in the cross direction,
wherein
the web includes a first side edge and a second side edge opposite to the first side edge in the cross direction, the end portion of the web includes the first side edge and the second side edge of the web, and the web position adjustment step further includes:
  photographing the first side edge and the second side edge of the web;
  outputting the positional information of the first and second side edges in the cross direction based on image data obtained by said photographing, and the position of the web in the cross direction is adjusted based on the outputted positional information.

* * * * *